United States Patent [19]

Ewall

[11] Patent Number: 5,522,794
[45] Date of Patent: Jun. 4, 1996

[54] METHOD OF TREATING HUMAN WOUNDS

[75] Inventor: Ralph Ewall, Newark, Del.

[73] Assignee: Hercules Incorporated, Wilmington, Del.

[21] Appl. No.: 260,940

[22] Filed: Jun. 16, 1994

[51] Int. Cl.$^6$ .................................................. A61F 13/00
[52] U.S. Cl. ................................. 602/41; 602/42; 602/56; 602/58
[58] Field of Search ................................. 602/41–43, 47, 602/48, 52, 54, 56, 57, 58, 59

[56] References Cited

U.S. PATENT DOCUMENTS

| | | | |
|---|---|---|---|
| 3,367,329 | 2/1968 | Dibelins . | |
| 3,419,006 | 12/1968 | King . | |
| 3,645,835 | 2/1972 | Hodgson . | |
| 3,664,343 | 5/1972 | Assarsson . | |
| 3,888,247 | 6/1975 | Stenvall | 128/155 |
| 3,972,328 | 8/1976 | Chen . | |
| 3,993,551 | 11/1976 | Assarsson et al. . | |
| 4,094,316 | 6/1978 | Nathanson . | |
| 4,181,127 | 1/1980 | Linsky et al. | 128/155 |
| 4,231,357 | 11/1980 | Hessner | 128/156 |
| 4,281,650 | 8/1981 | Spiegelberg . | |
| 4,413,621 | 11/1983 | McCracken et al. . | |
| 4,477,325 | 10/1984 | Osburn . | |
| 4,499,896 | 2/1985 | Heinecke . | |
| 4,538,603 | 9/1985 | Pawelchak et al. . | |
| 4,549,909 | 10/1985 | Thompson | 128/156 |
| 4,554,317 | 11/1985 | Behar et al. . | |
| 4,554,371 | 11/1985 | Majoie . | |
| 4,561,435 | 12/1985 | McKnight et al. | 128/156 |
| 4,598,004 | 7/1986 | Heinecke . | |
| 4,600,001 | 7/1986 | Gilman . | |
| 4,638,797 | 1/1987 | Merrill et al. . | |
| 4,641,643 | 2/1987 | Greer | 128/156 |
| 4,645,624 | 2/1987 | Ramm et al. . | |
| 4,649,909 | 3/1987 | Thompson . | |
| 4,657,006 | 4/1987 | Rawlings et al. . | |
| 4,738,257 | 4/1988 | Meyer et al. . | |
| 4,753,231 | 6/1988 | Lang et al. | 128/156 |
| 4,798,201 | 1/1989 | Rawlings et al. | 128/156 |
| 4,813,942 | 3/1989 | Alvarez | 604/290 |
| 4,875,473 | 10/1989 | Alvarez | 128/155 |
| 4,906,240 | 3/1990 | Reed et al. | 604/307 |
| 4,977,892 | 12/1990 | Ewall | 128/156 |
| 5,056,510 | 10/1991 | Gilman . | |
| 5,060,642 | 10/1991 | Gilman . | |
| 5,086,763 | 2/1992 | Hathman | 602/42 |
| 5,092,323 | 3/1992 | Riedel et al. | 602/54 |
| 5,106,629 | 4/1992 | Cartmell et al. . | |
| 5,139,861 | 8/1992 | Williams et al. | 428/288 |
| 5,145,676 | 8/1992 | Fahey, III et al. | 425/85.1 |
| 5,244,457 | 9/1993 | Karami et al. . | |
| 5,264,218 | 11/1993 | Rogozinski | 424/445 |
| 5,308,313 | 5/1994 | Karami et al. . | |

FOREIGN PATENT DOCUMENTS

| | | |
|---|---|---|
| 0106439 | 8/1983 | European Pat. Off. . |
| 0099758 | 2/1984 | European Pat. Off. . |
| 0106440 | 4/1984 | European Pat. Off. . |
| 0174803 | 3/1986 | European Pat. Off. . |
| 0190814 | 8/1986 | European Pat. Off. . |
| 0236104 | 9/1987 | European Pat. Off. . |
| 0304536 | 3/1989 | European Pat. Off. . |
| 0410009 | 1/1991 | European Pat. Off. . |
| 0236104 | 3/1987 | Germany . |
| 0304536A2 | 2/1988 | Germany . |
| 0106440 | 6/1983 | United Kingdom . |
| 0099758 | 7/1983 | United Kingdom . |
| 0106439 | 8/1983 | United Kingdom . |
| 8705206 | 9/1987 | WIPO . |

OTHER PUBLICATIONS

Balin et al., "The Effect of Oxygen Tension on the Growth & Metabolism of W1–38–Cells1,2", J. Cell. Physiol., 89:235–249.

Varghese et al., "Local Environment of Chronic Wounds Under Synthetic Dressings", Arch. Dermatol., vol. 122, Jan. 86, pp. 52–57.

Niinikoski et al., "Oxygen and Carbon Dioxide Tensions in Experimental Wounds", Surgery, Gynecology & Obstetrics, Dec. 71, vol. 133, pp. 1003–1007.

Knighton et al., Oxygen Tension Regulates the Expression of Angiogenesis Factor by Macrophages, Science 1983; vol. 221; pp. 1283–1285..

Kaufman et al., The Microclimate Chamber: The Effect of Continuous Topical Admin. of 96% Oxygen . . . ; J. of Trauma, 1983; vol. 23, No. 9; pp. 806–815.

Hunt et al., The Effect of Varying Ambient Oxygen Tensions on Wound Metabolism & Collagen Synthesis; 1972, vol. 135, pp. 561–567.

*Primary Examiner*—Corrine M. Maglione
*Assistant Examiner*—N. Kent Gring
*Attorney, Agent, or Firm*—Mark Goldberg; Martin F. Sloan

[57] ABSTRACT

Method of enhancing the healing of human wounds by controlling the microenvironment of the wound by sequentially applying to the wound dressings having moisture and oxygen permeabilities appropriate for the healing phases of the wound.

21 Claims, No Drawings

5,522,794

METHOD OF TREATING HUMAN WOUNDS

This invention relates to a method for treating Stages I and II type human wounds.

BACKGROUND OF THE INVENTION

The present invention relates to a wound healing process for treating Stages I and II human wounds that heal by secondary intention. Secondary intention means a healing by closure of a wound with granulations that form from the innermost base of the wound and proceed outwardly from the base and along the wound sides toward the surface of the wound. Secondary intention healing results in closure of the wound without closure by surgical intervention.

The classification of surface wound types by Stages is conventional. Four distinct stages are defined, primarily by their depth. A Stage I wound is a shallow wound that penetrates into but not through the epidermis. A stage II wound penetrates through the epidermis, and possibly into some subcutaneous tissue like fat, but not into muscle or bone. Examples of the Stages I and II wounds that often are healed by secondary intention include pressure sores, venus statis ulcers, and diabetic ulcers.

Prior art techniques and wound dressings for treating Stages I and II wounds have often extended, rather than reduced the time for healing. The ideal process for treating such dermal lesions provides many benefits, including maintaining tissue hydration at levels appropriate for the phase of wound healing, protecting against bacterial infiltration, eliminating premature scab formation, enhancing granulation, epithelial migration, and wound contraction and closing, all of which speed healing. To achieve these benefits, the process should provide the wound with a liquid and microorganism barrier, remove and prevent pooling of exudate while keeping the wound moist throughout most of the healing period, permit adequate oxygen ingress and carbon dioxide egress, and minimize trauma to surrounding and new tissue when removing the dressing.

Many prior art dressings provide some, but not all, of the above benefits. U.S. Pat. Nos. 4,598,004; 3,645,835; 4,638,797; 4,600,001; and 4,413,621 disclose wound dressings that are generally adequate for shallow wounds having low exudate levels. However, because of the low moisture vapor permeability rate (MVTR) of the dressings, they cannot remove exudate fast enough to prevent pooling under the dressing in applications to high exudate wounds.

Similarity the hydrogel dressings described in U.S. Pat. Nos. 4,554,317; 3,419,006; 3,993,551 and 3,664,343 have low exudate removal capabilities requiring frequent dressing changes.

To increase exudate removal, pouch dressings have been used, such as those described in U.S. Pat. Nos. 4,645,624; 4,499,896; and 4,657,006. These dressings effectively remove greater quantities of exudate, but are unable to manage the fluid of highly exudative wounds. Also these pouch dressings tend to separate from the skin prematurely.

Impermeable occlusive dressings have been used to give better adhesion and good absorption, as described in U.S. Pat. Nos. 3,972,328; and 4,538,603 and EP 0,190,814. These dressings comprise a layer of rubber based adhesive, compounded with absorbent material to absorb the exudate and retain it in the dressing. If not replaced frequently on highly exudative wounds, large quantities of exudate are entrapped next to the wound at a significant fluid pressure. Extensive skin macerations often occurs. Also the adherence of the dressings often fail, releasing entrapped fluid onto the patient.

U.S. Pat. Nos. 4,477,325 and 4,738,257 disclose occlusive rubber dressings, cross-linked to prevent degradation of the dressing into the wound during healing. Skin adhesion failures and leakage are not eliminated by these dressings.

To improve exudate management, and minimize the degradation of the dressing into the wound, island dressings have been used. As described in U.S. Pat. Nos. 4,561,435; 4,649,909 and 4,753,231, the island dressings absorb the exudate from the wound and evaporate it into the atmosphere through a water vapor permeable film These dressings do not manage exudate well for highly exudative wounds.

These and many other prior art dressings and healing methods have been described. However, not disclosed is a method incorporating the sequential use of dressings having different sequential moisture and as gas permeabilities to control the microenvironment of the wound to the conditions appropriate for healing during the particular phase of healing.

Healing of Stages I and II wounds, for purposes of the present invention, can be considered to take place in three phases. The phases are the same for Stages I and II, except in general the phases are longer time wise for Stage I.

There is a distinct optimal microenvironment for each healing phase that will produce the most rapid, quality healing. Sequentially the three phases are:

1. During phase 1, at the start of healing a Stage I or II wound, the wound exudes aqueous liquid, primarily blood and lymphatic fluid, at a rate of more about 5 ml per 24 hours. During the initial several days of healing, the most important factor is the removal of the exudate away from the wound. The optimum microenvironment enables the exudate to be drawn out of the wound as fast as it forms, readily pass through the dressing, and rapidly evaporate as it is exposed to the surrounding air. However, the exudate moisture is not removed so fast as to desiccate the wound. Also a high flow of oxygen from the outside air to the wound is necessary to promote new tissue growth, and carbon dioxide that forms in the wound area should readily pass to the outside air. The first phase continues until angiogenesis has begun to restore blood flow to the wound. Normally this requires about 5–15 days depending on the nature and location of the wound.

2. During phase 2 the wound size diminishes i.e. to about half the original size, angiogenesis continues restoring blood flow to the wound; and fibroblast migration and proliferation begin collagen generation and basement growth. For optimum 2nd phase healing, a high oxygen level, moist microenvironment is desired. The exudating of liquid decreases, normally to about 2 to 5 ml per 24 hours. Exudate removal should be sufficient to prevent pooling, but insufficient to desiccate the wound. The second healing phase continues until re-epithelization and re-mottling of the wound surface begins, normally about 5–15 days.

3. During phase 3 of healing re-epithelization is completed and wound approximation and closure takes place. Exudation decreases and then stops and the final scar tissue forms. The healing process is completed during phase 3. A high oxygen, low to dry moisture microenvironment is appropriate.

SUMMARY OF THE INVENTION

This invention relates to a secondary intention method of expediting the healing of Stage I and II human wounds. The method controls the microenvironment of the wound to provide, during the healing phases, the appropriate levels of exudate moisture, oxygen and carbon dioxide. This method comprises applying to the wound during the curing, a sequence of wound dressings having appropriate gas and exudate water vapor permeabilities for the particular phase of healing. This method also minimizes the possibility of wound contamination from microorganisms from outside sources, primarily bacteria, and from liquids, such as urinary and fecal excretions.

DESCRIPTION OF THE INVENTION

The present invention method of expediting the healing of a human wound comprises the sequential steps of:

(a) initially applying to the wound about every 2–7 days a first type wound dressing that is liquid and microorganism impermeable and has high moisture vapor transmission rate, or permeability (MVTR), and high oxygen permeability; and (b) thereafter applying to the wound about every 2–7 days, another type wound dressing that is liquid and microorganism impermeable and has low moisture vapor permeability (MVTR) and high oxygen permeability.

Preferably the first type wound dressing is applied at least until angiogenesis has begun, and the thereafter applied other type wound dressing is applied at least until exudation substantially ceases.

For the less severe, quickly healing wounds, an adequate microenvironment can be maintained by a single type of dressing during more than a single healing phase. A dressing having a high MVTR in the range of about 1000 to about 3000 g/m$^2$/24 hr. (at ambient pressure, 25° C. and 50% R.H.) and high gas permeability in the range of about 20,000 to about 70,000 cc/m$^2$/24 hr/atm (at 25° C. and 50% R.H.) is used for phase 1 and part or all of phase 2 healing. Thereafter healing is continued using a dressing having low MVTR, in the range of about 300 to about 2000 g/m$^2$/24 hrs. and high gas permeability in the range of about 40,000 to about 500,000 cc/m$^2$/24 hr/atm.

Preferably at least three types of dressings are used sequentially for the more severe wounds requiring more microenvironment control and differentiation.

In this preferred method dressings specific to the desired microenvironments of each of the three healing phases are used. The preferred method comprises sequentially using three dressings, all having liquid and microorganism impermeability, comprising: applying a first dressing every 2–7 days having high MVTR and high oxygen permeability; thereafter applying every 2–7 days a second intermediate dressing having medium MVTR and at least medium oxygen permeability; thereafter applying as frequently as needed a third dressing having low MVTR and high gas permeability. Most preferably the three dressing applications correspond substantially to wound healing phases 1, 2 and 3. Thus the second intermediate type wound dressing preferably is applied after the start of angiogenesis until about the time re-epithelization begins.

During phase 1 healing, the dressings used in the preferred method have MVTR in the range of about 1,500 to 3,000 g/m$^2$/day (24 hours) (measured at ambient pressure, 25° C. and 50% relative humidity). More preferably the dressings have MVTR in the range of about 1500 to about 2500 g/m$^2$/day; and most preferably about 1500 to 2000 g/m$^2$/day. They have oxygen permeability in the range of about 20,000 to about 70,000 cc/m$^2$/day/atm (25° C. and 50% R.H.); more preferably about 20,000 to about 50,000 cc/m$^2$/day/atm; and most preferably about 20,000 to about 30,000 cc/m$^2$/day/atm.

During phase 2 of healing the dressings used in the preferred method have MVTR in the range of about 1,000 to about 2,000 g/m$^2$/day; preferably in the range of about 1000 to about 1500 g/m$^2$/day; and most preferably in the range of about 1200 to about 1500 g/m$^2$/day. They have oxygen permeability in the range of about 40,000 to 100,000 cc/m$^2$/day/atm; more preferably from about 50,000 to about 70,000 cc/m$^2$/day/atm; and most preferably from about 60,000 to about 70,000 cc/m$^2$/day/atm.

During the phase 3 healing, the dressings used in the preferred method have MVTR in the range of about 300 to 800 g/m$^2$/day; preferably about 400 to 700 g/m$^2$/day; and most preferably about 500 to about 700 g/m$^2$/day. They have oxygen permeability in the range of about 60,000 to about 500,000 cc/m$^2$/day/atm; more preferably from about 70,000 to about 200,000 cc/m$^2$/day/atm; and most preferably from about 80,000 to about 150,000 cc/m$^2$/day/atm.

For very shallow low exudate Stage I wounds lower MVTRs and oxygen permeabilities may be used.

As used herein the term "gas" means oxygen and carbon dioxide. In practice the important gas permeability is oxygen permeability. When the oxygen permeability is correct, the carbon dioxide permeability will be more than adequate.

The basic components for suitable dressings to be used in the method of the present invention to provide the appropriate microenvironments are: (a) an exudate absorbing component such as a pad that will conduct exudate from the wound to; (b) a top cover sheet that will pass and evaporate the exudate moisture, and allow gas passage.

The wound dressings used in the method of the present invention can be of any shape and are flexible and conformable to the wound area. The preferred dressing is an island dressing having an absorbent pad with a non-adhering highly liquid permeable coating on the wound-side thereof, and a cover sheet on the opposite side of the pad away from the wound. The cover sheet is liquid and pathogen impermeable and is selected to have the desired MVTR and oxygen permeability. The pad, cover sheet and non-adhering layer are bonded together. They can be manufactured as a heat bonded laminated sheet stock, and cut to the desired pad size. On the outer side of the cover sheet of this preferred dressing is a pressure sensitive adhesive (PSA) coated attachment layer that is flexible and conformable, and binds the dressing to the skin. It is larger than the cover sheet/pad/non-adhering laminate, and has a central fenestration slightly smaller than the cover sheet/pad/non-adhering layer laminate. Typical attachment films are made of conventional polyester and polyester urethanes, copolyesters, polyether block imides, polyvinyl chloride, polyethylene, polypropylene, polybutene, latex rubbers and combinations of foam and film. A preferred film for use as the fenestrated attachment film is 20LF Type II reinforced polyurethane film from Gila River Corp., coated with a liquid and microorganism barrier PSA.

Another dressing ideally suited for use in the practice of the present method is an island dressing having a liquid, gas, and microorganism barrier adhesive base layer with a fenestrated area larger than the wound, which base layer adhesively attaches the dressing to the undamaged peripheral wound skin. Fitting tightly within the base layer fenestration is a laminate cover sheet/pad/non-adhering layer of the above described type, which will be in liquid conducting contact with the wound. The laminate withdraws exudate from the wound substantially as fast as it forms, while still maintaining the wound moist and undesiccated. On the outer side of the dressing is a fenestrated attachment layer not larger in area than the base layer. The fenestration is located over most of cover sheet and adhesively attached to its periphery and to the base layer. Alternatively, the cover sheet may be larger than the pad laminate and adhesively attach the laminate to the base layer. The pad fits tightly into the base layer fenestration; positioned to be in contact with the wound and no attachment layer is required.

This type dressing is constructed so that the cover sheet/ pad/non-adhering coating laminate can readily be striped off the base layer when desired for cleansing and/or medicating the wound; a new laminate can be put back in place covering the fenestrated area and adhering to the base layer. Normally the cover sheet and pad of the dressing is changed in this manner, without removal of the base layer, about every 2–7 days. The base layer may remain on the patient as long as it is functional, normally at least 10 days or more, and often for the entire healing period. During such changes the wound can be inspected. If indicated by the progress of healing, a cover sheet with different MVTR and oxygen permeability is selected to provide the desired wound exudate withdrawal and gas microenvironment for the particular healing phase.

Another suitable dressing type comprises an absorbent pad bonded to a cover sheet, which in turn has a second outer cover sheet adhesively bonded on the outer side thereof. The composition of the two (or more) cover sheets are selected to have the appropriate overall combined permeability to create the microenvironment desired for the phase of healing when the dressing is initially applied. Thereafter, if wound conditions require greater MVTR and/or oxygen permeability, the outer cover sheet can be removed from the dressing to give the dressing the permeabilities of the inner cover sheet.

In summary the preferred dressings used in the present method comprise as essential components, an absorbent pad and a cover sheet with appropriate permeabilities. Preferably these dressings also have fenestrated base layers to facilitate dressing changes.

Exemplary absorbent pads contain one or more layers of absorbent material in adequate quantity to keep the wound substantially drained of exudate. The pads and so the dressings, are capable of absorbing at least about 2 to about 20 cc/g of pad of exudate. Many non-toxic conventional known absorbent materials are readily available such as gauze, non-wovens, fluff cellulosic pulps, synthetic pulps, cotton, rayon and absorbent sponges. The pad size and shape will vary with the size and shape of the wound. It should be large enough to cover the wound. The pad can contain known absorbent particles, and medicaments such as antibiotics and wound healing stimulants.

Preferably the pad is treated to cover the wound side with a layer of material that renders the pad substantially non-adhering to the wound without impairing the pads absorbency. Suitable non-adhering layer treatments include lining the inner wound-facing side of the pad with a highly liquid-permeable non-sticky layer such as polymeric net, mesh or perforated film, or apertured polyethylene mesh such as "Delnet" P530 (a product of Applied Extrusion Technology, Inc.) Alternatively the pad inner side may be coated with a hydrogel material or other non-stick material.

The base layer can be any flexible, conformable sheet material that is a barrier to liquids, gas and microorganisms and that will adhere tightly to the skin throughout the desired time of wound-dressing usage. By "barrier" is meant that the base layer will not permit passage there through of significant amounts of liquids, gas or microorganisms. Preferably the base layer is sufficiently moisture absorbent to take up perspiration. The base layer can itself be sufficiently adhesive in nature, or a barrier pressure sensitive adhesive layer may be applied to the skin side of the base layer. Excellent base layers can be made of commercially available sheet material having the appropriate properties described above, and include rubber-based adhesive wafers that can be window cut to accommodate the pad. Ideal materials are "DUO-DERM" compounded rubber sheet material, a product of Bristol-Meyers-Squib Corp.; and "Variseal" A 15, A 15 Mod. and A 52 adhesive films, products of Veriseal Corp.

For ease in handling, a conventional release liner covering the adhesive skin side of the dressing is used during handling before application. W89-SP/P silicone coated release liner (a product of Mead Paper Products, West Chicago, Ill.) in a overlap or plowfold configuration is an excellent release liner.

The cover sheet is the dressing component essential for maintaining the desired wound microenvironment by controlling the liquid, oxygen and carbon dioxide levels of the wound microenvironment. Thus the cover sheet is liquid and pathogen impermeable, and is permeable to moisture vapor, oxygen and carbon dioxide. The cover sheet is selected to have a MVTR and an oxygen permeability that will enable the dressing to pass out and evaporate the desired aqueous portion of the exudate and pass the appropriate amount of oxygen into the wound microenvironment while passing out carbon dioxide as it forms. For the sequential dressing wound healing method of the present invention, a variety of cover sheets, or combinations of cover sheets, are used that impart to the dressings the desired MVTRs and oxygen permeabilities during progress in healing. The following Table 1 lists a number of cover sheet films suitable for use in the present invention, and their MVTR's and gas permeances, which dictate the permeabilities of the dressings. Permeance is permeability per mil of film thickness.

TABLE 1

| FILM | MVTR | O$_2$ PERM/CO$_2$ PERM | | THICKNESS MILS |
|---|---|---|---|---|
| Microporous polyolefin PM-3 (Consolidated Thermoplastics Corp.) | 3800 | 21,700,000(a) | 21,700,000(a) | 0.8 |
| Microporous ppolyolefin X-25813-24-1 (Hercules Incorporated) | 950 | 8,640,000)a) | 8,640,000(a) | 4.8 |
| Microporous polyolefin X-27448-44-4 (Hercules Incorporated) | 360 | 294,500 | 1,473,000 | 4.2 |
| Microporous polyolefin X28244-13-4 (Hercules Incorporated) | 150 | 357,000 | 357,000 | 7.3 |
| Microporous polyolefin X28244-13-3 (Hercules Incorporated) | 140 | 138,000 | 138,000 | 7.2 |
| Silicone (Surgitec Corp.) | — | >100,000 | 646,500 | 1.3 |
| Styrenebutadienestyrene (Consolidated | ~200 | 64,000 | 214,000 | 1.0 |

TABLE 1-continued

| FILM | MVTR | O$_2$ PERM/CO$_2$ PERM | THICKNESS MILS |
|---|---|---|---|
| Thermoplastics Corp.) | | | |
| Polyether block imide MF-827 (Bertek Corp.) | 2000 | 49,800 — | 1.0 |
| Copolyester MF-3548 (Bertek Corp.) | 2175 | 33,800 >20,000,000 | 1.5 |
| Polyurethane 946B (PCF-MED Corp.) | 1400 | 20,600 167,500 | 1.5 |
| Polyetherpolyurethane KM1391-02 (Semex Corp.) | 960 | 14,675 84,200 | 2.7 |
| Copolyester KM1353-06 (Semex Corp,) | 870 | 13,000 126,500 | 3.0 |
| Copolyester Med 5002 (Fasson Corp.) | 390 | 10,418 — | 2.0 |
| Copolyester MF-325 (Bertek Corp.) | 300 | 9,600 111,500 | 0.7 |
| Low Density Polyethylene (USI Corp.) | ~30 | 2,800 12,000 | 3.0 |
| Polyesterpolyurethane KM1393-00 (Semex Corp.) | 330 | 1,270 10,200 | 4.0 |
| Cellophane P4T (Flexel Corporation) | 2300 | 17 <40 | 1.5 |

(a)measured by an experimental method for high permeable films.

Units for MVTR are g/sq.m./24 hrs. at ambient pressure, 25 deg. C. and 50% R.H. and for Permeance are cc/sq.m./24 hrs/atm. at 25 deg. C. and 50% R.H.

EXAMPLE 1

Three Sample dressings 4"×4" are prepared, each having a top cover sheet 4"×4" coated on its inner surface with a conventional liquid and microorganism barrier PSA that is highly moisture and gas permeable. The cover sheets are centrally bonded to a 3"×3" pad ¼" thick of "Synpulp" 232.100 absorbent fibrous pad material. "Synpulp" 232.100 is fluffed wood pulp intimately blended with "Pulpex" polypropylene/polyethylene fibrous material treated with a wetting agent, made by Hercules Incorporated. Each pad has the bottom covered with non-adhering "Delnet" P530 polyethylene mesh from Applied Extrusion Technology, Inc. Each pad has an absorbency of over 10 cc/g of pad. The dressing is adhesively attached to the peripheral wound skin at the 1" periphery of the cover sheet.

Table 2 lists the cover sheets and dressing permeabilities of Samples 1–3. In Table 2, and Table 3 of Example 2, the oxygen permeabilities are in cc/m$^2$/24hrs/atm, and the MVTRs are in g/m$^2$/24 hrs. at ambient pressure; each at 25° C. and 50% R.H.

TABLE 2

| Sample | Cover Sheet | Dressing Permeabilities | |
|---|---|---|---|
| | | Oxygen | MVTR |
| 1. | Copolyester film MF-3548 from Bertek Corp. | 34,000 | 2200 |
| 2. | "Pebax" MF-827 from Bertek Corp. | 50,000 | 2000 |
| 3. | Microporous Polyethylene film X27448 from Hercules Incorporated | 300,000 | 360 |

Samples 1–3 dressings are applied to Stage I highly exudative dermal lesion decubitus ulcer wounds sequentially to each wound as follows:

Sample 1—one every third day for 9 days, during which time angiogenesis and fiberblast proliferation begins.

Sample 2—one every third day for 9 days, during which time collagen formation and wound surface approximation occur, and re-epithelization and re-mottling of the wound surface begin.

Sample 3—one every fifth day for 15 days, during which time re-epithelization occurs across the fully granulated wound bed and the wound becomes closely approximated.

After this 33 days sequential treatment the wounds are substantially healed.

Treating Stage II wounds sequentially the same as the above exemplified Stage I wound treatments, but with slightly longer treatment periods for each phase, gives similar good results.

EXAMPLE 2

Three dressing Samples 4–6 are prepared like dressing Samples 1–3 of Example 1, except that a second outer top cover sheet 3½"×3½ is adhesively bonded to the top of each cover sheet ½" in from the sides. The second outer top cover sheets of Samples 4–6 are copolyester film Med 5002 from Fasson Corp. Table 3 lists the permeabilities of Samples 4–5 dressings.

TABLE 3

| Sample No. | Dressing Permeabilities | |
|---|---|---|
| | Oxygen | MVTR |
| 4. | 7,700 | 390 |
| 5. | 8,600 | 390 |
| 6. | 10,000 | 360 |

Sample dressings 4–6 are applied to low exudative partial thickness dermal ulcer lesion wounds in the following sequence:

Sample 4—dressings, one every third day for six days;
Sample 5—dressings, one every third day for six days;
Sample 6—one dressing, for 4 days.

After this 16 day sequential dressings treatments the wounds are closely approximated, with fully granulated wound beds, substantially fully healed.

EXAMPLE 3

Three dressing Samples 7–9 are prepared like dressing Samples 1–3 of Example 1, except that fenestrated base layers 4"×4" and ¼" thick of "Variseal" A-15 rubber based adhesive sheet material from Veriseal Corp. are adhesively attached to the wound side of each cover sheet. The fenestrations are slightly larger than 3"×3". The pads, with non-adhering "Delnet" P530 on the wound sides, fit snugly into the fenestrations. The Samples 7–9 have the same permeabilities as Samples 1–3 respectively.

Ulcer wounds of the type described in Example 1 are sequentially treated with Samples 7–9 dressings at the same frequencies and for the same time periods as in Example 1. However, when the dressings are changed, only the cover sheets with the pads are stripped off the base layers and replaced with Samples 1–3 cover sheet/pad dressings, with one exception. On the 12th day (4th dressing change) Sample 8 dressings, including the base layer, are replaced. Thus, only on the 4th and 9th dressing removals are the base layers removed from the patients skin, thereby minimizing wound peripheral skin damage. After this 33 day sequential dressings treatment, the wounds are substantially healed.

What is claimed:

1. A method of expediting healing of a wound comprising:
   initially applying to the wound about every 2 to 7 days a first type wound dressing that is liquid and microorganism impermeable and has a high moisture vapor permeability and high oxygen permeability, the first type wound dressing comprising, at 25° C. and 50% relative humidity, a moisture vapor transmission rate of about 1,000 to about 3,000 g/m$^2$/day at ambient pressure, and an oxygen permeability of about 20,000 to about 70,000 cc/m$^2$/day/atm; and
   thereafter applying to the wound about every 2 to 7 days another type wound dressing that is liquid and microorganism impermeable and has a low moisture vapor permeability and high oxygen permeability, the another type wound dressing comprising, at 25° C. and 50% relative humidity, a moisture vapor transmission rate of about 300 to about 2,000 g/m$^2$/day at ambient pressure, and an oxygen permeability of about 40,000 to about 500,000 cc/m$^2$/day/atm.

2. The method according to claim 1, wherein said wound comprises a Stage I wound.

3. The method according to claim 1, wherein said wound comprises a Stage II wound.

4. The method according to claim 1, wherein said wound comprises at least one of a human Stage I wound and a human Stage II wound.

5. The method according to claim 1, wherein the first type wound dressing is applied at least until angiogenesis has begun.

6. The method according to claim 1, wherein the another type wound dressing is applied until exudation substantially ceases.

7. The method according to claim 1, wherein the first type wound dressing is applied at least until angiogenesis has begun, and the another type wound dressing is applied until exudation substantially ceases.

8. The method according to claim 1, wherein after application of the first type wound dressing and before application of the another type wound dressing, an intermediate second type wound dressing is applied to the wound every 2 to 7 days, the intermediate second type wound dressing comprising medium moisture vapor permeability and at least medium oxygen permeability.

9. The method according to claim 8, wherein said intermediate second type wound dressing is applied to the wound subsequent to initiation of angiogenesis until about initiation of re-epithelization.

10. The method according to claim 8, wherein the first type wound dressing is applied for a period of about 5 to about 15 days, and the second type wound dressing is applied for a period of about 5 to about 15 days.

11. The method according to claim 10, wherein the first type wound dressing is applied for substantially a period of time when phase 1 healing of the wound occurs, the second type wound dressing is applied for substantially a period of time when phase 2 healing of the wound occurs, and the another type wound dressing is applied for at least a part of a period of time when phase 3 healing of the wound occurs.

12. The method according to claim 8, wherein at least one of the first type wound dressing, the second type wound dressing and the another type wound dressing comprises a liquid, gas and microorganism barrier base layer including a fenestration area, the fenestration area being larger than the wound, the base layer including adhesive to adhesively attach the at least one of the first type wound dressing and the another type wound dressing to a peripheral skin area of the wound so that the at least one of the first type wound dressing, the second type wound dressing and the another type wound dressing may remain on the patient through several dressing changes.

13. The method according to claim 8, wherein at least one of the first type wound dressing, the second type wound dressing and the another type wound dressing comprises an absorbent pad and at least one liquid and moisture impermeable, moisture vapor and oxygen permeable cover sheet permitting evaporation of exudate water and allowing oxygen to enter and carbon dioxide to egress from an area surrounding the wound, and wherein the absorbent pad comprises a wound facing side and a side opposite said wound facing side, and the at least one cover sheet is positioned adjacent to the side opposite the wound facing side.

14. The method according to claim 1, wherein at least one of the first type wound dressing and the another type wound dressing comprises an absorbent pad and at least one liquid and moisture impermeable, moisture vapor and oxygen permeable cover sheet permitting evaporation of exudate water and allowing oxygen to enter and carbon dioxide to egress from an area surrounding the wound, and wherein the absorbent pad comprises a wound facing side and a side opposite the wound facing side, and the at least one cover sheet is positioned adjacent to the side opposite the wound facing side.

15. The method according to claim 14, wherein the absorbent pad and the at least one cover sheet are heat bonded together and are constructed and arranged to be in exudate conducting contact with the wound.

16. The method according to claim 1, wherein at least one of the first type wound dressing and the another type wound dressing comprises a liquid, gas and microorganism barrier base layer including a fenestration area, the fenestration area being larger than the wound, the base layer including adhesive to adhesively attach the at least one of the first type wound dressing and the another type wound dressing to a peripheral skin area of the wound so that the at least one of the first type wound dressing and the another type wound dressing may remain on the patient through several dressing changes.

17. A method of expediting healing of a wound comprising:
   initially applying to the wound about every 2 to 7 days a first type wound dressing that is liquid and microorganism impermeable and has a high moisture vapor permeability and high oxygen permeability, the first type wound dressing comprising, at 25° C. and 50% relative humidity, a moisture vapor transmission rate of about 1,500 to about 3,000 g/m²/day at ambient pressure, and an oxygen permeability of about 20,000 to about 70,000 cc/m²/day/atm;

thereafter applying to the wound about every 2 to 7 days a second type wound dressing that has a medium moisture vapor permeability and at least medium oxygen permeability, the second type wound dressing comprising, at 25° C. and 50% relative humidity, a moisture vapor transmission rate of about 1,000 to about 2,000 g/m²/day at ambient pressure, and an oxygen permeability of about 40,000 to about 100,000 cc/m²/day/atm; and thereafter applying to the wound about every 2 to 7 days another type wound dressing that is liquid and microorganism impermeable and has a low moisture vapor permeability and high oxygen permeability, the another type wound dressing comprising, at 25° C. and 50% relative humidity, a moisture vapor transmission rate of about 300 to about 800 g/m²/day at ambient pressure, and an oxygen permeability of about 60,000 to about 500,000 cc/m²/day/atm.

18. A method of expediting healing of a wound comprising:

initially applying to the wound about every 2 to 7 days a first type wound dressing that is liquid and microorganism impermeable and has a high moisture vapor permeability and high oxygen permeability, the first type wound dressing comprising, at 25° C. and 50% relative humidity, a moisture vapor transmission rate of about 1,500 to about 3,000 g/m²/day at ambient pressure, and an oxygen permeability of about 20,000 to about 50,000 cc/m²/day/atm;

thereafter applying to the wound about every 2 to 7 days a second type wound dressing that has a medium moisture vapor permeability and at least medium oxygen permeability, the second type wound dressing comprising, at 25° C. and 50% relative humidity, a moisture vapor transmission rate of about 1,000 to about 1,500 g/m²/day at ambient pressure, and an oxygen permeability of about 50,000 to about 70,000 cc/m²/day/atm; and thereafter applying to the wound about every 2 to 7 days another type wound dressing that is liquid and microorganism impermeable and has a low moisture vapor permeability and high oxygen permeability, the another type wound dressing comprising, at 25° C. and 50% relative humidity, a moisture vapor transmission rate of about 400 to about 700 g/m²/day at ambient pressure, and an oxygen permeability of about 70,000 to about 400,000 cc/m²/day/atm.

19. A method of expediting healing of a wound comprising:

initially applying to the wound about every 2 to 7 days a first type wound dressing that is liquid and microorganism impermeable and has a high moisture vapor permeability and high oxygen permeability, the first type wound dressing comprising, at 25° C. and 50% relative humidity, a moisture vapor transmission rate of about 1,500 to about 2,000 g/m²/day at ambient pressure, and an oxygen permeability of about 20,000 to about 30,000 cc/m²/day/atm;

thereafter applying to the wound about every 2 to 7 days a second type wound dressing that has a medium moisture vapor permeability and at least medium oxygen permeability, the second type wound dressing comprising, at 25° C. and 50% relative humidity, a moisture vapor transmission rate of about 1,200 to about 1,500 g/m²/day at ambient pressure, and an oxygen permeability of about 60,000 to about 70,000 cc/m²/day/atm; and thereafter applying to the wound about every 2 to 7 days another type wound dressing that is liquid and microorganism impermeable and has a low moisture vapor permeability and high oxygen permeability, the another type wound dressing comprising, at 25° C. and 50% relative humidity, a moisture vapor transmission rate of about 500 to about 700 g/m²/day at ambient pressure, and an oxygen permeability of about 80,000 to about 150,000 cc/m²/day/atm.

20. A method of expediting healing of a wound comprising:

initially applying to the wound about every 2 to 7 days a first type wound dressing that is liquid and microorganism impermeable and has a high moisture vapor permeability and high oxygen permeability;

thereafter applying to the wound about every 2 to 7 days another type wound dressing that is liquid and microorganism impermeable and has a low moisture vapor permeability and high oxygen permeability;

at least one of the first type wound dressing and the another type wound dressing comprises an absorbent pad and at least one liquid and moisture impermeable, moisture vapor and oxygen permeable cover sheet permitting evaporation of exudate water and allowing oxygen to enter and carbon dioxide to egress from an area surrounding the wound, and wherein the absorbent pad comprising a wound facing side and a side opposite the wound facing side, and the at least one cover sheet is positioned adjacent to the side opposite the wound facing side; and the absorbent pad is capable of absorbing from about 2 to about 20 cc/g of pad of wound exudate.

21. A method of expediting healing of a wound comprising:

initially applying to the wound about every 2 to 7 days a first type wound dressing that is liquid and microorganism impermeable and has a high moisture vapor permeability and high oxygen permeability;

thereafter applying to the wound about every 2 to 7 days a second type wound dressing that has a medium moisture vapor permeability and at least medium oxygen permeability;

thereafter applying to the wound about every 2 to 7 days another type wound dressing that is liquid and microorganism impermeable and has a low moisture vapor permeability and high oxygen permeability;

at least one of the first type wound dressing, the second type wound dressing and the another type wound dressing comprises an absorbent pad and at least one liquid and moisture impermeable, moisture vapor and oxygen permeable cover sheet permitting evaporation of exudate water and allowing oxygen to enter and carbon dioxide to egress from an area surrounding the wound, and wherein the absorbent pad comprises a wound facing side and a side opposite the wound facing side, and the at least one cover sheet is positioned adjacent to the side opposite the wound facing side; and the absorbent pad is capable of absorbing from about 2 to about 20 cc/g of pad of wound exudate.

* * * * *